(12) United States Patent
Philippens et al.

(10) Patent No.: US 6,360,784 B1
(45) Date of Patent: Mar. 26, 2002

(54) VALVED CONNECTOR AND METHOD OF USE

(75) Inventors: Frans Philippens, Beek (NL); Craig F. Borchard, Mendota Heights, MN (US); Jill Guimont; Tim Hauch, both of Minneapolis, MN (US); Dan Sheehan, Maple Grove, MN (US); Robert Spencer; Mary Robischon, both of Minneapolis, MN (US); Joanna Pierce, New Brighton, MN (US); Patrick Johnson, Robbinsdale, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/470,020

(22) Filed: Dec. 22, 1999

(51) Int. Cl.$^7$ ................................................. B65B 3/04
(52) U.S. Cl. ................................ 141/2; 141/21; 141/27
(58) Field of Search ............................... 141/2, 21, 25, 141/26, 27, 98, 18; 604/7, 9, 187, 247, 323, 407, 409, 246; 137/511

(56) References Cited

U.S. PATENT DOCUMENTS

| 4,210,173 | A | * | 7/1980 | Choksi et al. ............ 137/512.3 |
| 4,534,758 | A | * | 8/1985 | Akers et al. .................... 604/85 |
| 5,176,658 | A | * | 1/1993 | Ranford ....................... 604/247 |
| 5,188,603 | A | * | 2/1993 | Vaillancourt ................. 604/131 |
| 5,240,035 | A | * | 8/1993 | Aslanian et al. ............. 137/501 |
| 5,267,964 | A | * | 12/1993 | Karg ........................... 604/141 |
| 5,395,324 | A | * | 3/1995 | Hinrichs et al. ............... 604/86 |
| 5,586,629 | A | * | 12/1996 | Shoberg et al. ................ 141/21 |
| 5,665,074 | A | * | 9/1997 | Kelly .......................... 604/247 |
| 5,957,883 | A | * | 9/1999 | Lin ............................... 604/36 |
| 6,056,727 | A | * | 5/2000 | O'Neil ....................... 604/183 |
| 6,059,747 | A | * | 5/2000 | Bruggeman et al. .......... 604/49 |
| 6,096,011 | A | * | 8/2000 | Trombley, III et al. ...... 604/256 |
| 6,102,897 | A | * | 8/2000 | Lang .......................... 604/246 |

* cited by examiner

Primary Examiner—Gregory L. Huson
Assistant Examiner—Peter deVore
(74) Attorney, Agent, or Firm—Thomas G. Berry; Curtis D. Kinghorn; Stephen W. Bauer

(57) ABSTRACT

A device and method for aseptically filling high pressure reservoirs in medicament pumps is disclosed. The device preferably includes a filter, a connector having a one-way valve and a filling tube with a terminal needle. The filter is connectable to a pharmacy prepared syringe containing a drug to be transferred to the reservoir of the IDIP. The filter is connected to the connector. The connector has a first and a second inlet port fluidly connected to an outlet port. A one-way valve is located in the connector "upstream" of the point where the two inlet ports connect to the outlet port. The filling tube is connectable to the outlet port. In use, a pharmacy syringe is connected to the first inlet port. A filling syringe is connected to the second inlet port. The filling tube is connected to the outlet port. The terminal needle of the filling tube is passed through the patient's skin and into the IDIP. The practioner draws the drug into the filling syringe from the pharmacy syringe through the connector. When the filling syringe is full, the practioner pushes the filling syringe plunger in thereby forcing the drug out of the outlet port, through the filling tube and terminal needle into the reservoir of the IDIP. The one-way valve prevents the drug from re-entering the pharmacy syringe.

41 Claims, 6 Drawing Sheets

VALVED CONNECTOR AND METHOD OF USE

BACKGROUND OF THE INVENTION

1. Field of the Invention

The invention relates to medicament pumps implantable in a body and more specifically to a device for filling high pressure reservoirs in medicament pumps implantable in a body.

2. Description of the Related Art

The implantable drug infusion pump (IDIP) has provided physicians with a powerful tool for administering a wide variety of drugs and other agents, such as pain killers, nerve growth factor, and anti-spasticity drugs, to very particularized sites within a patient's body, such as the intrathecal region of the spinal column. The IDIP has also freed some patients from the restrictions of typical intravenous drug infusion systems that typically include a wheeled cart that must be pulled around behind the patient.

An IDIP is ordinarily surgically implanted subcutaneously in the patient's abdomen. The IDIP has an internal reservoir for storing the drug or agent. After implantation, the drug or agent is delivered to a selected site in the patient's body via a catheter that is attached to the pump and tunneled subcutaneously to the selected site. Many medical applications calling for an IDIP require very minute dosages or drug or agent to be delivered to the selected site over a period of time. For example, dosages of 100 $\mu$l over a span of twenty-four hours are not uncommon.

Before the IDIP can be implanted in the patient's body, it must be filled with the applicable drug or agent. For many long-term applications, the IDIP may have to be refilled while the pump is still implanted within the patient's body. This is normally done by passing the drug or agent through a hypodermic needle that has been pierced through the patient's skin and coupled to the subcutaneously disposed IDIP.

A prior art system for refilling and IDIP is shown in FIG. 1. The prior art system 10 includes a pharmacy syringe 12, a filter 14, a filling tube 16, and an IDIP 18. Filter 14 has an inlet 20 that is coupled to the discharge outlet 22 of the pharmacy syringe 12. Filter 14 is preferably any of a number of well known types that prevent bacteria, sediments or other undesirable particles from passing through it and into the IDIP 18.

The discharge orifice 24 of the filter 14 is coupled to the inlet end 26 of the filling tube 16. The filling tube 16 terminates in a needle 28. Pharmacy syringe 12 has a plunger 30. As the plunger 30 of the pharmacy syringe 12 is depressed, drug flows from the pharmacy syringe 12 through the filter 14 and the filling tube 16 and into the IDIP 18.

As shown in FIG. 2, the needle 28 enters the IDIP 18 through a septum 32. Septum 32 provides a fluid barrier for a chamber 34 within IDIP 18. Chamber 34 is fluidly connected to a reservoir 36 through a manifold 38. Reservoir 36 is typically formed within a bellows structure 40 that is connected to manifold 38. An outer shell 42 is attached to the manifold 38 around the bellows structure 40. A sealed pressure chamber 44 is formed between outer shell 42 and bellows structure 40.

A propellant gas is place in pressure chamber 44. The propellant gas acts as a pressure-providing means to the bellows structure 40 that biases the bellows structure 40 to discharge the drug or other agent stored in the reservoir 36. The propellant gas used to drive such a "gas driven" IDIP is a fluid that is in phase change between a liquid state and a gas state when, i.e., in equilibrium between phases at around 37 degrees (Celsius), which is the usual temperature of the human body. In programmable IDIPs such as the SynchroMed pump manufactured and sold by Medtronic, Inc. of Minneapolis, Minn., the propellant gas is chosen to provide a pressure on the bellows structure of about 4 p.s.i. In this device, the metering of the drug or other agent out of the device is done through a peristaltic mechanism.

In constant rate IDIPs such as the IsoMed® pump manufactured and sold by Medtronic, Inc. of Minneapolis, Minn., the propellant gas is chosen to provide a pressure on the bellows structure of about 32 p.s.i. In this device, the metering of the drug or other agent is done through capillary tube that provides a relatively constant flow rate of drug or other agent out of the reservoir 36. The reason for a higher pressure in the pressure chamber 44 in a constant rate pump with a capillary tube flow restrictor is that this higher pressure reduces the variability in flow rates of the drug or other agent due to atmospheric conditions such as barometric pressure.

As mentioned above, when refilling the IDIP, the drug or other agent is passed from a pharmacy syringe 12 through the filter 14 and the filling tube 16 and into the IDIP 18 where it passes into the reservoir 36. However, the drug or other agent must enter the reservoir 36 at a pressure sufficient to overcome the pressure bias on the reservoir 36 from the propellant gas in the pressure chamber 44. In the case of the IsoMed® pump, the drug or other agent must be delivered to the reservoir 36 at a pressure higher than 32 p.s.i.

Due to the principles of hydraulics, this 32 p.s.i. pressure is applied over the entire cross-sectional area of the plunger 30. When refilling an IDIP 18, typically the entire reservoir capacity of the IDIP is refilled. A typical IDIP 18 may have a reservoir volume of 20 ml, 40 ml or 60 ml. To refill an IDIP 18 with, for example, a 60 ml reservoir, a pharmacy typically prepares 60 ml of the drug or other agent and places it in a pharmacy syringe 12 corresponding in size to the amount of drug or other agent to be refilled, in this case, a 60 ml syringe. The 60 ml pharmacy syringe 12 could be coupled directly to the system 10 through the coupling of discharge outlet 22 and inlet 20.

As is well known, the cross-sectional area of the plunger 30 of a relatively small syringe such as a 10 ml syringe is smaller than the cross-sectional area of a larger syringe such as a 60 ml syringe. As a result, the force needed to apply 32 p.s.i. to drug or other agent in a pharmacy syringe 12 is determined by multiplying 32 p.s.i. by the crosssectional area of the plunger 30. In the case of a 60 ml syringe, this total force is on the order of 25 pounds. This is a larger force than many people are able to generate with their hands. On the other hand, because the cross-sectional area of a 10 ml syringe is about a quarter of the cross-sectional area of a 60 ml syringe, the total force needed to apply apply 32 p.s.i. to drug or other agent in a pharmacy syringe 12 is about 6 pounds. This force is well within the range of force that most people can generate with their hands.

As a result, many practioners, when refilling large reservoir pumps such as the 60 ml reservoir pumps, require the pharmacy to place the 60 ml of the drug or other agent to be refilled into several smaller syringes such as 10 or 20 ml syringes instead of in one large syringe. These smaller syringes allow the practioner to apply the drug or other agent to the reservoir 36 even in pumps such as the IsoMed® pump that have relatively high gas propellant pressures in the pressure chambers 44. Unfortunately, using several smaller syringes instead of one large syringe means that each pharmacy syringe 12 must be attached and disconnected from the inlet 20 each time instead of once as would be the case for the larger syringe. With this increased number of connections and disconnections, there is an increased chance of infection entering the system or other problems occurring.

In view of the foregoing, it is desirable to provide a system that allows the practioner to easily provide the drug or other agent to the reservoir 36 of the IDIP 18 while at the same time minimizing the number of times the sterile connection between the pharmacy syringe 12 and the system 10 is broken. The present invention is directed to overcoming the aforementioned disadvantage. Throughout this disclosure, like elements, wherever referred to are referenced by like reference numbers.

SUMMARY OF THE INVENTION

A device and method for aseptically filling high pressure reservoirs in medicament pumps is disclosed. The device preferably includes a filter, a connector having a one-way valve and a filling tube with a terminal needle. The filter is connectable to a pharmacy prepared syringe containing the drug or other agent to be transferred to the reservoir of the IDIP. The filter is in turn connected to the connector.

The connector has a first and a second inlet port and an outlet port. The two inlet ports are fluidly connected to the outlet port. The first inlet port is connectable to the pharmacy syringe containing the drug or other agent to be transferred to the reservoir of the IDIP. The second inlet port is connectable to a filling syringe. The filling syringe is preferably of a size that allows the practioner to easily apply sufficient force to the drug or other agent to overcome the pressure bias on the reservoir of the IDIP and allow the drug or other agent to be admitted to the reservoir to refill the reservoir.

A one-way valve is located in the connector "upstream" of the point where the two inlet ports connect to the outlet port on the first inlet port leg of the connector. The one-way valve allows fluid to flow from this syringe to either the second inlet port or the outlet port. But, the one-way valve prevents fluid from flowing from either the second inlet port or the outlet port through the first inlet port. The filling tube is connectable to the outlet port.

In use, a syringe containing the drug or other medicament to re-fill the IDIP is connected to the first inlet port. A filling syringe is connected to the second inlet port. The filling tube is connected to the outlet port. The terminal needle of the filling tube is passed through the patient's skin and through the septum of the IDIP where the drug or other agent may pass into the chamber and ultimately into the reservoir of the IDIP.

The practioner draws the drug or other agent into the filling syringe from the pharmacy prepared syringe by pulling the plunger of the filling syringe back. This causes drug in the pharmacy prepared syringe to move from the pharmacy prepared syringe through the one-way valve through the connector to the filling syringe. When the filling syringe is full, the practioner pushes the filling syringe plunger in thereby forcing the drug or other agent out of the outlet port, through the filling tube and terminal needle into the chamber of the IDIP and ultimately into the reservoir of the IDIP. The one-way valve prevents the drug or other agent from re-entering the pharmacy prepared syringe. Since the filling syringe is typically smaller than the pharmacy prepared syringe, several cycles of filling and emptying the filling syringe as described above will need to be performed in order to transfer the drug or other agent from the pharmacy prepared syringe to the reservoir of the IDIP.

BRIEF DESCRIPTION OF THE DRAWINGS

Advantages of the invention will become apparent upon reading the following detailed description and references to the drawings in which.

DESCRIPTION OF THE PREFERRED EMBODIMENT

Figure 1:
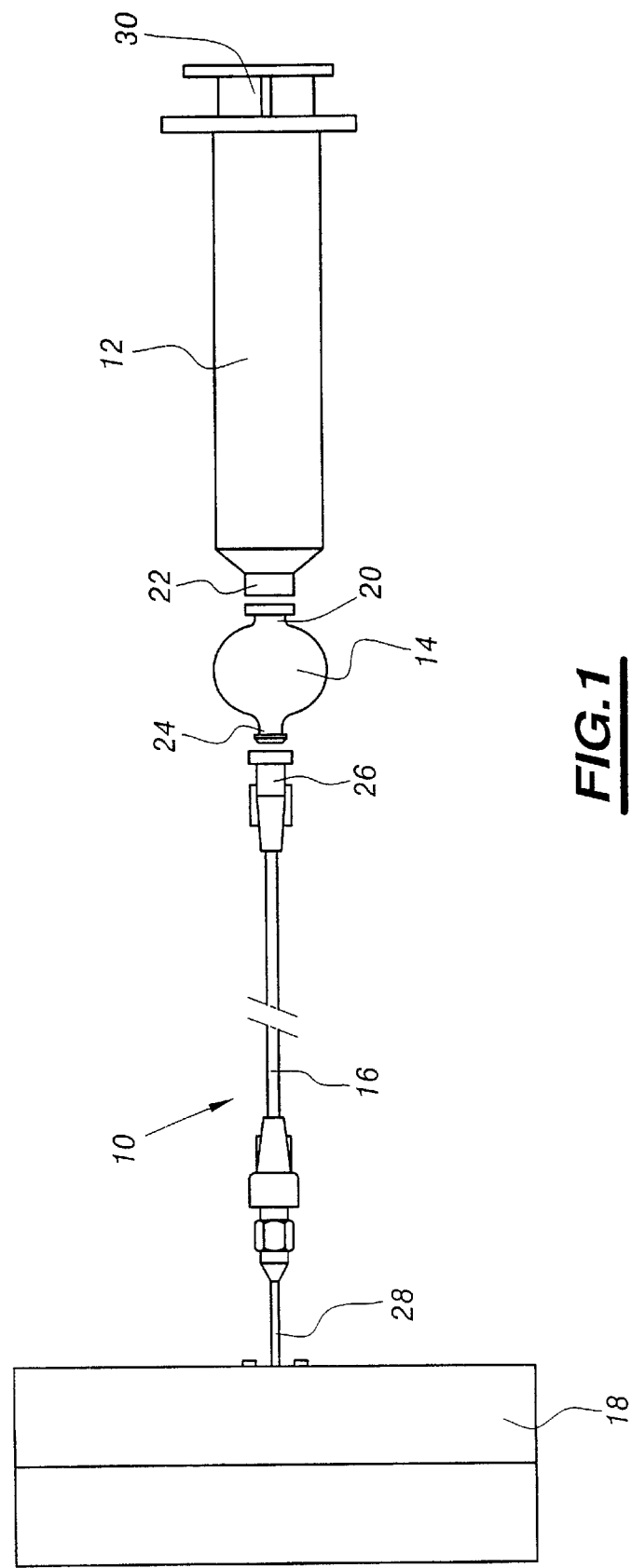
FIG. 1 is a side view of an exemplary prior art IDIP filling system.
Figure 2:
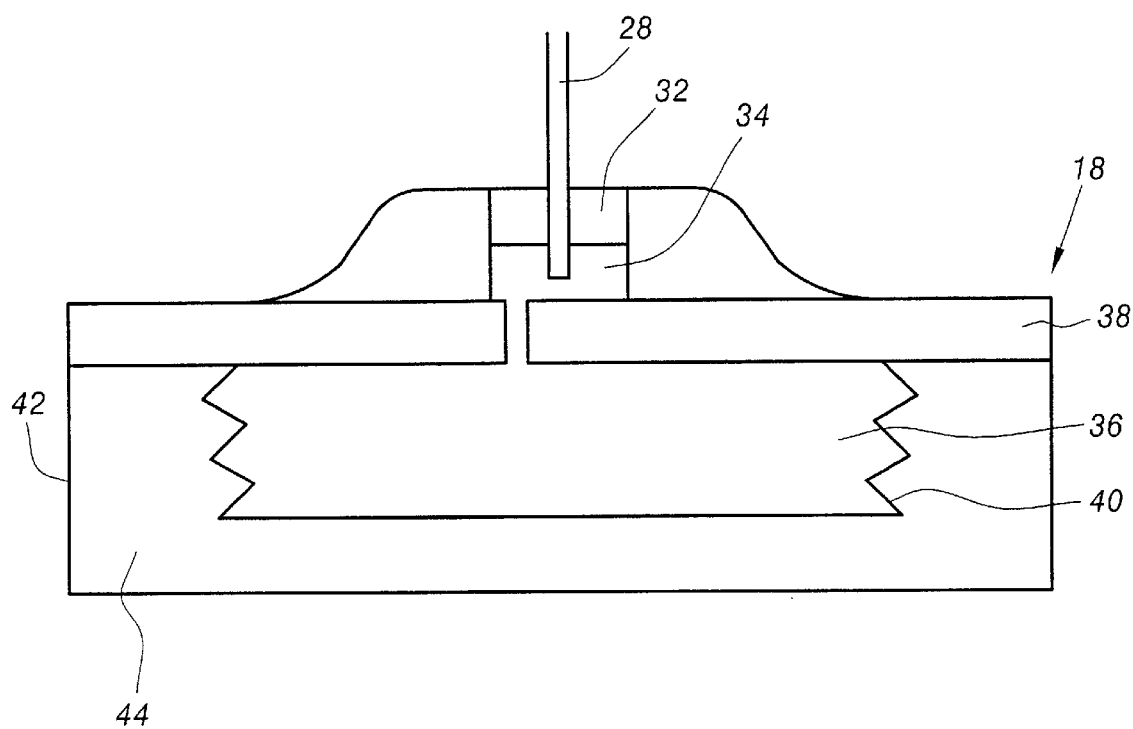
FIG. 2 is a side cross-sectional view of an exemplary prior art IDIP.
Figure 3:
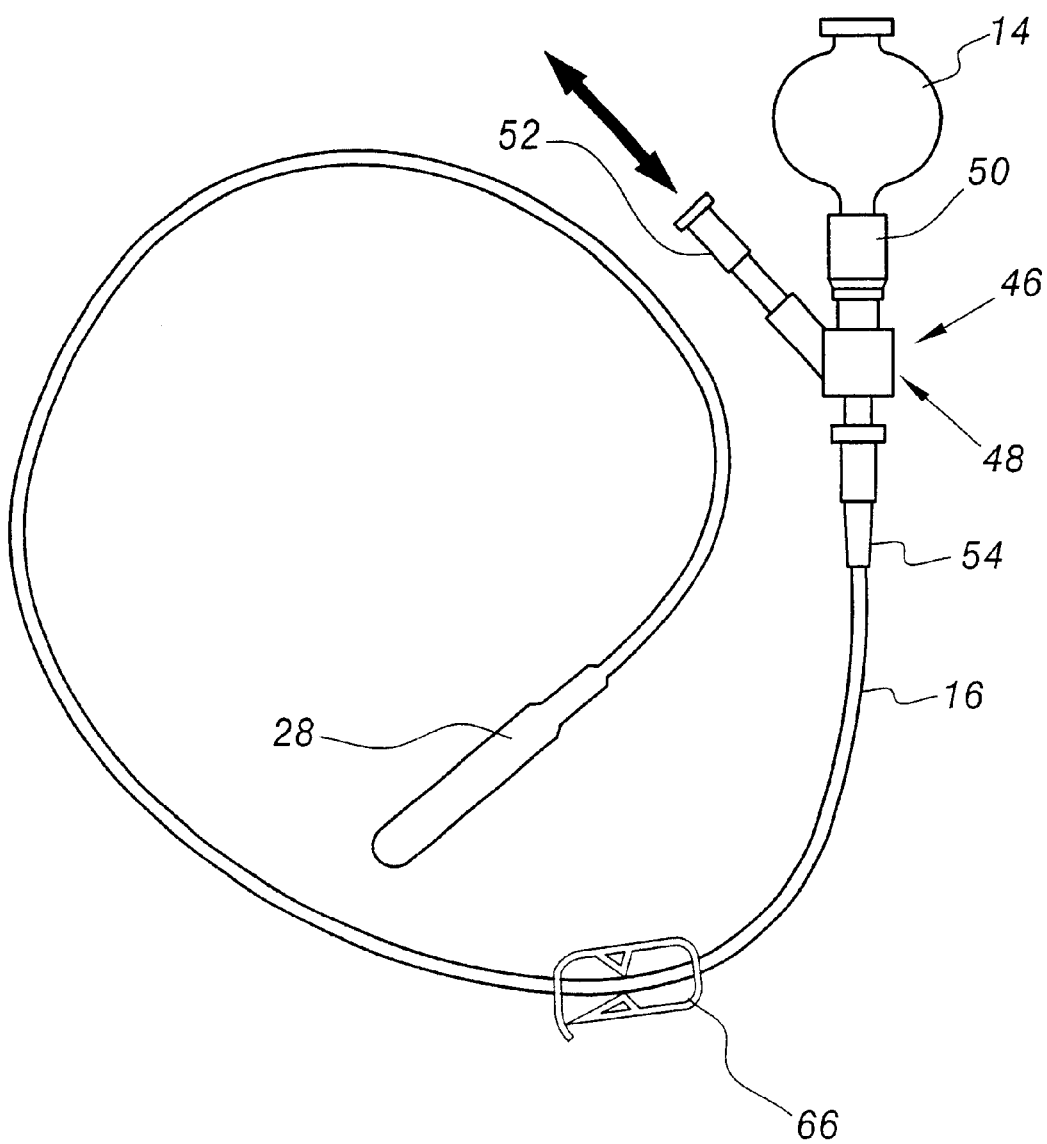
FIG. 3 is a side view of the preferred embodiment of the IDIP filling system.
Figure 4:
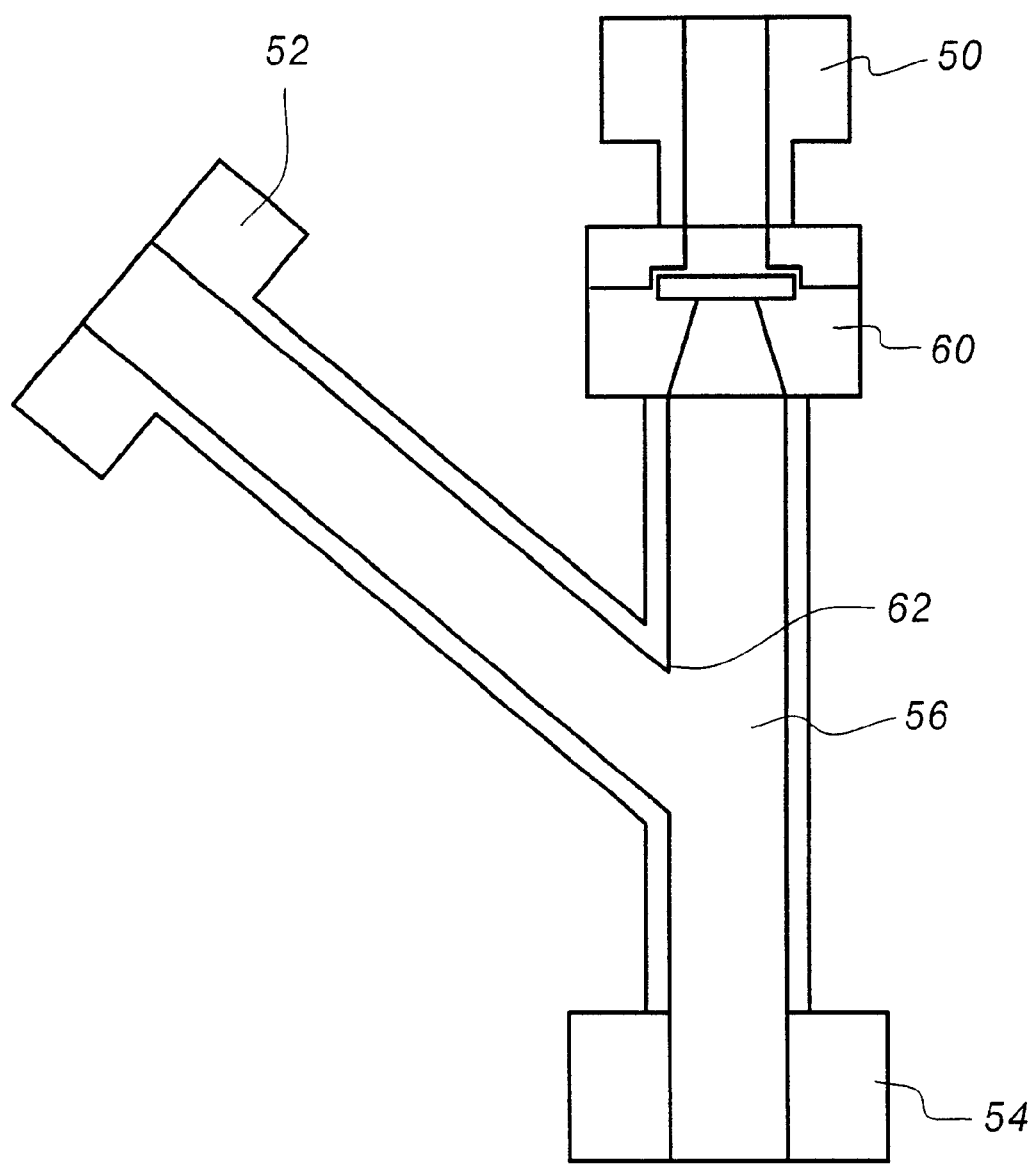
FIG. 4 is a side cross-sectional view of the connector of FIG. 3.

FIG. 3 depicts an exemplary preferred embodiment of an IDIP filling system 46 according to the disclosed invention. The system 46 includes a filter 14, a connector 48 and a filling tube 16. Connector 48 has a first inlet port 50, a second inlet port 52 and an outlet port 54. The first and second inlet ports 50, 52 are fluidly connected to the outlet port 54 through central lumen 56. The first inlet port 50 preferably has a luer lock connection that allows it to be connected to a filter 14 or a pharmacy syringe 12 containing the drug or other agent to be transferred to the reservoir 36 of the IDIP 18.

The second inlet port 52 also preferably has a luer lock connection that allows it to be connected to a filling syringe 58.

A one-way valve 60 is located in the central lumen 56 "upstream" of the point 62 where the first and second inlet ports 50, 52 join together to connect to the outlet port 54. One-way valve 60 allows fluid to flow only from and not to the pharmacy syringe 12. This allows the drug or other agent to flow from the pharmacy syringe 12 to either the second inlet port 52 or the outlet port 54. Fluid flow back through the one-way valve 60 to the pharmacy syringe 12 is prevented by the one-way valve 60.

The preferred structure for one-way valve 60 is a flexible disk valve as is well known in the art. Although the preferred embodiment for one-way valve 60 is a flexible disk valve, other one-way valves may be used as will occur to those skilled in the art. These include, but are not limited to, ball valves, duck-billed valves, slit valves and umbrella valves.

The outlet port 54 and the filling tube 16 also each preferably has a luer lock connector that allows the filling tube to be connected to the outlet port 54. Although luer lock connectors have been described as the preferred way of connecting syringes 12, 58 and filling tube 16 to the system 10, any other method of connections may be used as will be clear to those skilled in the art.

Figure 5:
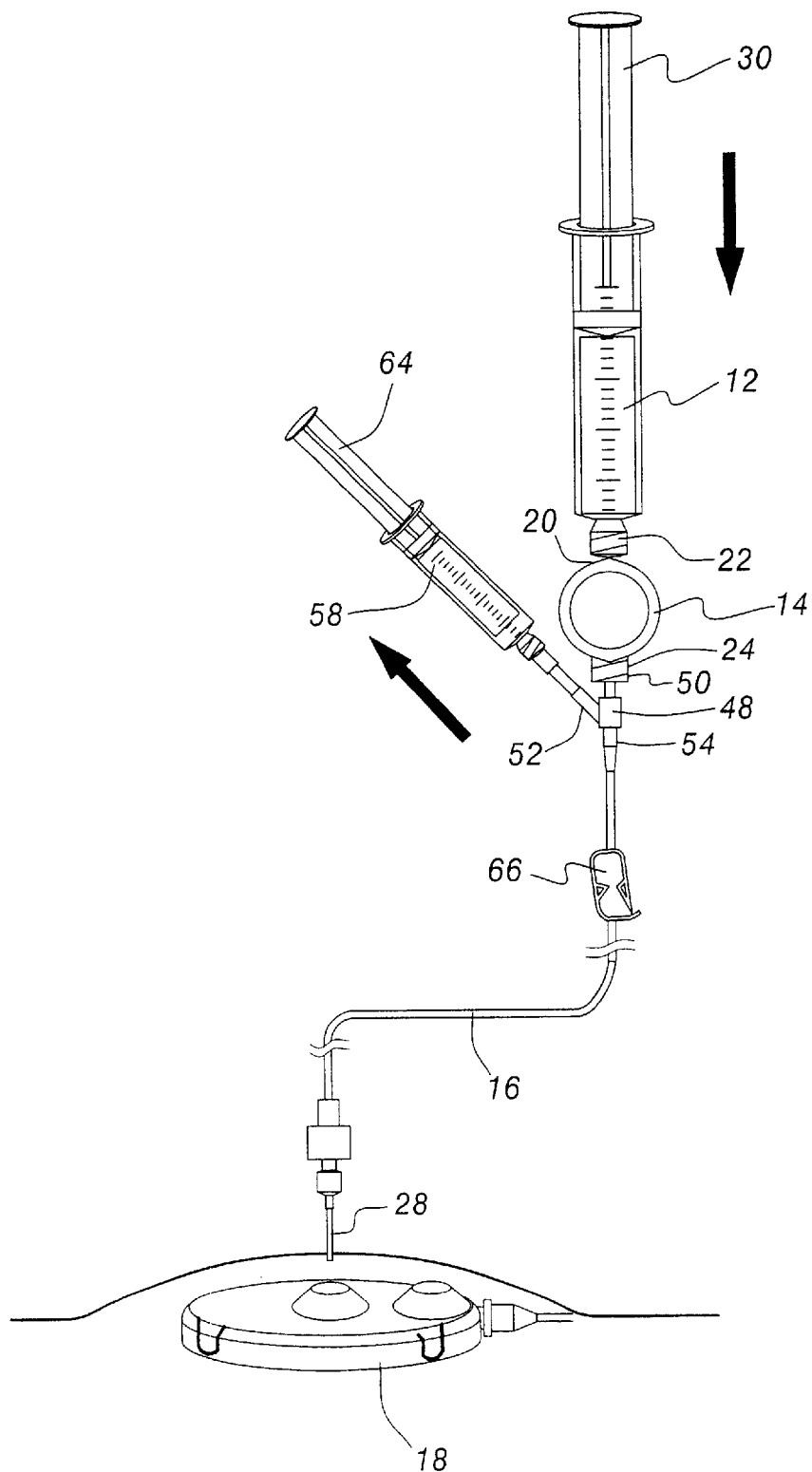
FIG. 5 is a side view of the IDIP filling system of FIG. 3 with the pharmacy and filling syringes attached and the drug or other agent being transferred from the pharmacy syringe to the filling syringe.
Figure 6:
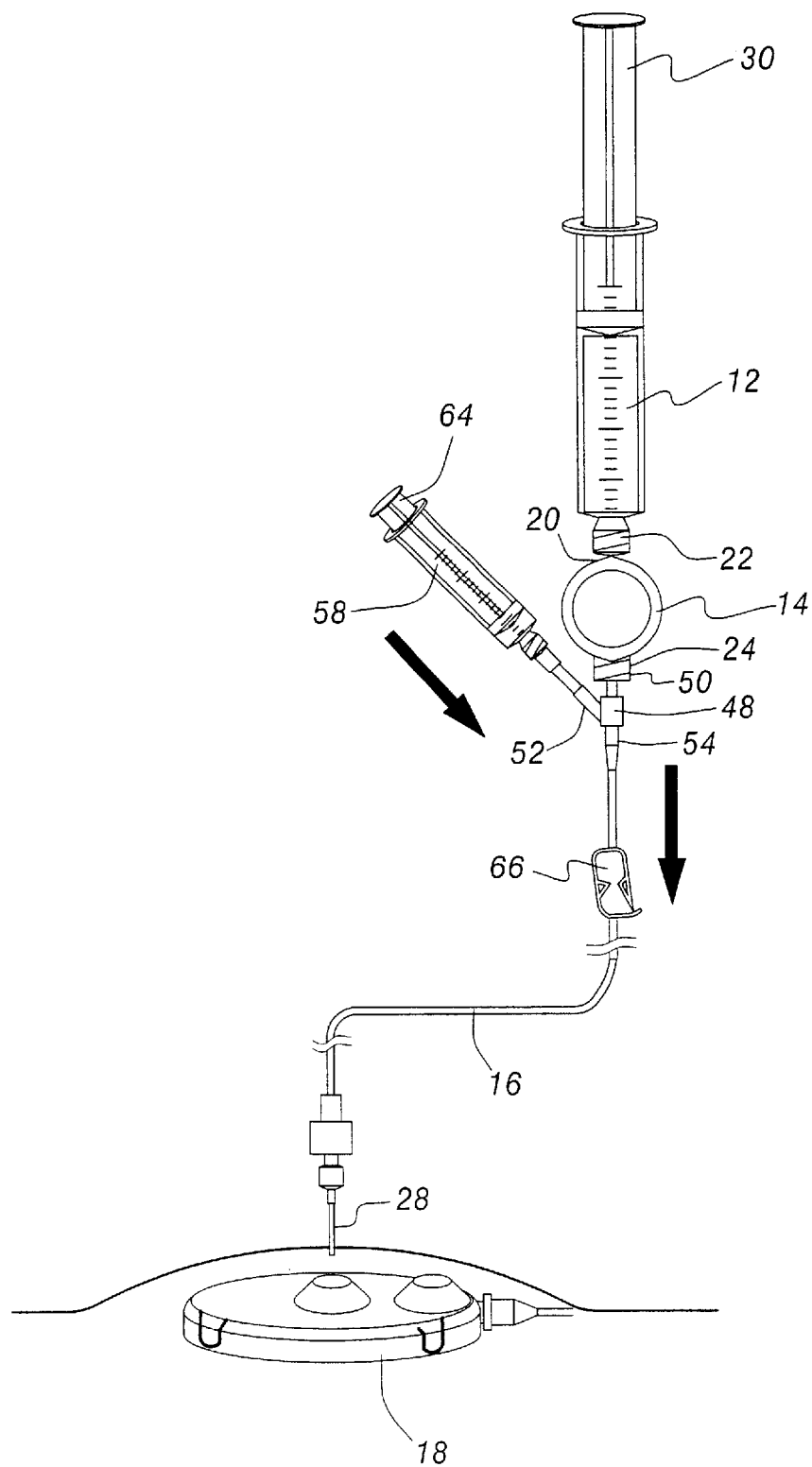
FIG. 6 is a side view of the IDIP filling system of FIG. 3 with the pharmacy and filling syringes attached and the drug or other agent being transferred from the filling syringe to the IDIP.

The use of the system 46 is shown in FIGS. 5 and 6. As is shown in FIG. 5, a pharmacy syringe 12 containing the drug or other medicament to re-fill the IDIP 18 is connected to inlet 20 of filter 14 through discharge outlet 22. Discharge outlet 24 of filter 14 is connected to the first inlet port 50. A filling syringe 58 is connected to the second inlet port 52. The filling syringe 58 is preferably of a size that allows the practioner to easily apply sufficient force to the drug or other agent to overcome the pressure bias on the reservoir of the IDIP and allow the drug or other agent to be admitted to the reservoir to refill the reservoir.

The filling tube 16 is connected to the outlet port 54. The terminal needle 28 of the filling tube 16 is passed through the patient's skin and through the septum 32 of the IDIP 18 into the chamber 34.

Because the pharmacy syringe 12 is full, the plunger 30 of pharmacy syringe 12 is in its fully displaced position. At this stage, filling syringe 58 is empty so that its plunger 64 is in its fully engaged position.

To transfer drug from the pharmacy syringe 12 to the filling syringe 58, plunger 30 is depressed while plunger 64 is withdrawn. As a result, drug or other agent in pharmacy syringe 12 passes through filter 14, where undesireable contaminants are removed, arid one-way valve 60 to the filling syringe 58.

When filling syringe 58 is full, clamp 66 is opened and plunger 64 is depressed. One-way valve 60 prevents the drug or other agent in filling syringe 58 from passing back into pharmacy syringe 12. Instead, the drug or other agent passes out of filling syringe 58 through the central lumen 56 to and out of outlet port 54, into filling tube 16 where the drug or other agent leaves the needle 28 in chamber 34. There, the drug or other agent passes from the chamber 34 to the reservoir 36 under pressure supplied by the filling syringe 58. The drug or other agent under pressure overcomes the bias on the bellows structure 40 by the gas propellant and fills the reservoir 36.

When the drug or other agent in the filling syringe 58 has been expelled, if there is additional drug or other agent remaining in the pharmacy syringe 12 the transfer process of moving drug or other agent from the pharmacy syringe 12 to the filling syringe 58 must be repeated. To repeat the process, a clamp 66 is preferably placed on filling tube 16 between the outlet port 54 and the needle 28. Before repeating the transfer process, clamp 66 is locked in a closed configuration. The locked clamp 66 prevents drug in the IDIP 18 from returning from the IDIP 18 to the system 46 since the drug in IDIP 18 is under pressure from the propellant gas in the pressure chamber 44.

Once clamp 66 is closed, plunger 30 is depressed while plunger 64 is withdrawn as described above to transfer the drug or other agent from the pharmacy syringe 12 to the filling syringe 58. This process continues until all the drug or other agent in the pharmacy syringe 12 has been transferred to the reservoir 36 of the IDIP 18.

Many modifications and variations may be made in the techniques and structures described and illustrated herein without departing from the spirit and scope of the present invention. For example, the first and second inlets 50, 52 may be formed to connector 48 through a variety of configurations, including but not limited to, the first inlet port 50 and the outlet port 54 being collinear with the second inlet port being attached to the connector 48 at any angle, acute, obtuse or right. As another example, first and second inlet ports 50, 52 may be formed as opposing legs of a "Y" with the outlet port 54 formed on the base of the "Y". Other configurations will occur to those skilled in the art. Further, although filter 14 is part of the preferred embodiment of the system 46, filter 14 may also be eliminated as desired. Additionally, filter 14 or filling tube 16 or both may be made as an integral part of connector 48. Other changes and modifications will occur to those skilled in the art. Accordingly, the techniques and structures described and illustrated herein should be understood to be illustrative only and not limiting upon the scope of the present invention.

What is claimed is:

1. An implantable pump filling system comprising:
    a connector having a central lumen, a first inlet port, a second inlet port and an outlet port, the first and second inlet ports and the outlet port being fluidly connected to the central lumen, the connector having a one-way valve located in the central lumen between the first inlet port an d the point where the second inlet port connects to the central lumen, the one-way valve biased to allow fluid to pass only from the first inlet port to the central lumen, the one-way valve being selected from the group consisting of a flexible disk valve, a duck-billed valve, a slit valve and an umbrella valve;
    a filling tube having a proximal and a distal end, the proximal end connected to the outlet port; and
    a clamp disposed between the filling tube distal end and the outlet port to prevent fluid flow between the distal end and the outlet port when the clamp is activated.

2. The implantable pump filling system of claim 1 further comprising a filter, the filter connected to the first inlet port.

3. The implantable pump filling system of claim 2 wherein the filter is integrally connected to the first inlet port.

4. The implantable pump filling system of claim 1 wherein the filling tube is integrally connected to the outlet port.

5. The implantable pump filling system of claim 1 wherein the filling tube includes a terminal needle.

6. The implantable pump filling system of claim 1 wherein the first inlet port has a luer lock connection.

7. The implantable pump filling system of claim 1 wherein the second inlet port has a luer lock connection.

8. The implantable pump filling system of claim 1 wherein the outlet port has a luer lock connection.

9. The implantable pump filling system of claim 1 wherein the one-way valve comprises a flexible disk valve.

10. The implantable pump filling system of claim 1 wherein the clamp is manually actuatable between an open position in which the clamp does not prevent flow between the distal end and the outlet port, and an activated position in the clamp prevents flow between the distal end and the outlet port.

11. The implantable pump filling system of claim 1 wherein the first and second inlet ports and the outlet port each have luer lock connections, the connector comprising a Y-type connector.

12. A method of transferring fluid from a first syringe to a second syringe and from the second syringe to a reservoir of an implantable pump, the second syringe having a plunger, comprising the steps of:
    providing an implantable pump filling system comprising:
        a connector having a central lumen, a first inlet port, a second inlet port and an outlet port, the first and second inlet ports and the outlet port being fluidly connected to the central lumen, the connector having a one-way valve located in the central lumen between the first inlet port and the point where the second inlet lumen connects to the central lumen, the one-way valve biased to allow fluid to pass only from the first inlet port to the central lumen; and a filling tube connected to the outlet port, the filling tube having a terminal needle;

connecting the first syringe to the first inlet port;

connecting the second syringe to the second inlet port, the plunger of the second syringe being fully depressed;

placing the terminal needle in an implantable pump in fluid communication with the reservoir of the implantable pump;

drawing fluid from the first syringe into the second syringe by drawing out the plunger of the second syringe;

depressing the plunger of the second syringe whereby fluid is expelled from the second syringe out of the connector and through the filling tube into the implantable pump reservoir.

13. The method of claim 12 wherein the implantable pump filling system further comprises a filter, the filter connected to the first inlet port.

14. The method of claim 13 wherein the filter is integrally connected to the first inlet port.

15. The method of claim 12 wherein the filling tube is integrally connected to the outlet port.

16. The method of claim 12 wherein the first inlet port has a luer lock connection.

17. The method of claim 12 wherein the second inlet port has a luer lock connection.

18. The method of claim 12 wherein the out let port has a luer lock connection.

19. The method of claim 12 wherein the one-way valve is chosen from the group consisting of a flexible disk valve, a ball valve, a duck-billed valve, a slit valve and an umbrella valve.

20. The method of claim 12 further comprising activating a clamp disposed along the filling tube between the outlet port and terminal needle to prevent fluid flow between the terminal needle and the outlet port.

21. A combination comprising:

an implantable drug pump having a reservoir and a refill port; and an implantable pump filling system comprising a connector having a central lumen, a first inlet port, a second inlet port and an outlet past, the first and second inlet ports and the outlet port being fluidly connected to the central lumen, the connector having a one-way valve located in the central lumen between the first inlet port and the point where the second inlet port connects to the central lumen, the one-way valve biased to allow fluid to pass only from the first inlet port to the central lumen; and a filling tube having a proximal and a distal end, the proximal end connected to the outlet port and the distal end adapted for fluid communication with the reservoir of the implantable, drug pump for filling the reservoir.

22. The combination of claim 21 wherein the implantable pump filling system further comprises a filter, the filter connected to the first inlet port.

23. The combination of claim 22 wherein the filter is integrally connected to the first inlet port.

24. The combination of claim 21 wherein the filling tube is integrally connected to the outlet port.

25. The combination of claim 21 wherein the filling tube includes a terminal needle.

26. The combination of claim 21 wherein the one-way valve is selected from the group consisting of a flexible disk valve, a ball valve, a duck-billed valve, a slit valve and an umbrella valve.

27. The combination of claim 21 wherein the one-way valve is selected from the group consisting of a flexible disk valve, a duck-billed valve, a slit valve and an umbrella valve.

28. The combination of claim 21 wherein the reservoir of the implantable drug pump has a pressure bias against which the reservoir is refilled by a drug or other agent, the combination further comprising:

a pharmacy syringe containing a drug or other agent to be transferred to the reservoir, the pharmacy syringe being connected to the first inlet port; and a filling syringe of a size that facilitates applying sufficient force to the drug or other agent to overcome the pressure bias of the reservoir and allow the drug or other agent to be admitted to the reservoir to refill the reservoir.

29. The combination of claim 28 wherein the first and second inlet ports and the outlet port each have luer lock connections, the connector comprising a Y-type connector.

30. The combination of claim 28 wherein the one-way valve is chosen from the group consisting of a flexible disk valve, a duck-billed valve, a slit valve and an umbrella valve.

31. The combination of claim 30 wherein the one-way valve comprises a flexible disk valve.

32. The combination of claim 28 wherein the filling tube includes a terminal needle.

33. The combination of claim 28 wherein the implantable pump filling system further comprises a clamp disposed between the filling tube distal end and the outlet port to prevent fluid flow between the distal end and the outlet port when the clamp is activated.

34. The combination of claim 33 where the clamp is manually actuatable between an open position in which the clamp does not prevent flow between the distal end and the outlet port, and an activated position in the clamp prevents flow between the distal end and the outlet port.

35. An implantable pump filling system for filling a pressurized reservoir of an implantable pump, the system comprising:

a connector having a central lumen, a first inlet port, a second inlet port and an outlet port, the first and second inlet ports and the outlet port being fluidly connected to the central lumen, the connector having a one-way valve located in the central lumen between the first inlet port and the point where the second inlet port connects to the central lumen, the one-way valve biased to allow fluid to pass only from the first inlet port to the central lumen such that fluid entering from the second inlet port is prevented from passing to the first inlet port;

a filling tube having a proximal and a distal end, the proximal end connected to the outlet port;

a pharmacy syringe containing a drug or other agent to be transferred to the reservoir, the pharmacy syringe being connected to the first inlet port; and a filling syringe of a size that facilitates applying sufficient force to the drug or other agent to overcome the pressure bias of the reservoir and allow the drug or other agent to be admitted to the reservoir to refill the reservoir.

36. The implantable pump filling system of claim 35 wherein the first and second inlet ports and the outlet port each have luer lock connections, the connector comprising a Y-type connector.

37. The implantable pump filling system of claim 36 wherein the one-way valve is chosen from the group consisting of a flexible disk valve, a duck-billed valve, a slit valve and an umbrella valve.

38. The implantable pump filling system of claim 37 wherein the one-way valve comprises a flexible disk valve.

39. The implantable pump filling system of claim 35 the filling tube includes a terminal needle.

40. The implantable pump filling system of claim 35 wherein the implantable pump filling system further comprises a clamp disposed between the filling tube distal end and the outlet port to prevent fluid flow between the distal end and the outlet port when the clamp is activated.

41. The implantable pump filling system of claim 40 wherein the clamp is manually actuatable between an open position in which the clamp does not prevent flow between the distal end and the outlet port, and an activated position in the clamp prevents flow between the distal end and the outlet port.

* * * * *